United States Patent
Chiang et al.

(10) Patent No.: US 8,670,821 B2
(45) Date of Patent: Mar. 11, 2014

(54) ELECTROENCEPHALOGRAM SIGNAL PROCESSING METHOD

(75) Inventors: Ching-Tai Chiang, Pingtung (TW);
Rong-Ching Wu, Kaohsiung (TW);
Chen-Sen Ouyang, Kaohsiung (TW);
Li-Ju Huang, Kaohsiung (TW);
Rei-Cheng Yang, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 339 days.

(21) Appl. No.: 13/285,736

(22) Filed: Oct. 31, 2011

(65) Prior Publication Data

US 2012/0184869 A1    Jul. 19, 2012

(51) Int. Cl.
*A61B 5/04*    (2006.01)

(52) U.S. Cl.
USPC ............ 600/544; 600/545; 702/190; 702/196

(58) Field of Classification Search
USPC ........................... 600/544, 545; 702/190, 196
See application file for complete search history.

(56) References Cited

U.S. PATENT DOCUMENTS

| | | | | |
|---|---|---|---|---|
| 6,073,040 | A * | 6/2000 | Kiyuna .......................... | 600/409 |
| 7,630,757 | B2 * | 12/2009 | Dorfmeister et al. .......... | 600/544 |
| 2010/0198098 | A1 * | 8/2010 | Osorio et al. .................. | 600/544 |
| 2013/0060125 | A1 * | 3/2013 | Zeman et al. .................. | 600/409 |

FOREIGN PATENT DOCUMENTS

TW    201102047    1/2011

OTHER PUBLICATIONS

Tong, et al., "Waveform-Preserving Blind Estimation of Multiple Independent Sources" IEEE Transactions on Signal Processing (Jul. 1993), pp. 2461-2470, vol. 41, No. 7.

* cited by examiner

*Primary Examiner* — Navin Natnithithadha
*Assistant Examiner* — Etsub Berhanu
(74) *Attorney, Agent, or Firm* — Muncy, Geissler, Olds & Lowe, P.C.

(57) ABSTRACT

An electroencephalogram signal processing method includes a recording step, a retrieving step, a removing step and a synthesizing step. The recording step retrieves EEG signal components of a testee via a plurality of electrodes, wherein the EEG signal components serve as an input signal. The retrieving step filters the input signal to obtain a predetermined frequency band signal, and subtracts the predetermined frequency band signal from the input signal to obtain a difference signal. The removing step performs an independent component analysis operation between the difference signal and a separating matrix to obtain an analysis signal, generates a separating pseudo inverse and an independent analysis signal, and performs a matrix operation between the separating pseudo inverse and the independent analysis signal to obtain a corrected signal. The synthesizing step adds the corrected signal and the predetermined frequency band signal together to obtain an output signal.

6 Claims, 6 Drawing Sheets

ELECTROENCEPHALOGRAM SIGNAL PROCESSING METHOD

BACKGROUND OF THE INVENTION

1. Field of the Invention

The present invention generally relates to an electroencephalogram signal processing method and, more particularly, to an EEG signal processing method that preserves predetermined frequency band signals before removing interfering signals thereof.

2. Description of the Related Art

Electroencephalogram (EEG) data is a curved diagram formed by weak biological signals of a human brain, and is used to diagnose cerebrovascular diseases or epilepsy. However, EEG signals tend to be distorted under interferences caused by artifact sources. As an example, EEG signals are seriously interfered by eye movement, blink, muscle movement, electrocardiogram (EKG), power line noises, etc, leading to contamination of the EEG signals. In light of this, it is required to remove the interfering signals from the EEG signals before the EEG signals can be applied to medical diagnosis or brain status detection.

Conventionally, contaminated EEG signals are visually checked to find out interfering signals contained therein, and the interfering signals are removed from the EEG signals to complete the EEG signal processing method. Alternatively, U.S. Pat. No. 5,513,649 entitled "ADAPTIVE INTERFERENCE CANCELER FOR EEG MOVEMENT AND EYE ARTIFACTS" discloses a sensor that can detect and remove the interfering signals, which are caused by artifact sources, from EEG signals. The EEG signals without interfering signals are output as an output signal. Finally, a feedback operation is performed on the output signal to obtain needed EEG signals. However, when the EEG signals are in a small amount or seriously interfered by muscle movement or power line noises, removing the interfering signals from the contaminated EEG signals may lead to a loss of some useful information, making the processed EEG signals not useful for clinical diagnosis.

To solve the problem, other EEG signal processing methods were proposed to remove interfering signals from EEG signals based on Independent Component Analysis (ICA) algorithm. The ICA-based EEG signal processing methods can be seen in an IEEE paper entitled "Waveform-preserving blind estimation of multiple independent sources" or in a Taiwan patent with publication No. 201102047. In the Taiwan patent, independent components are retrieved from EEG data for blind signal separation (BSS). Namely, the independent components are retrieved for an ICA operation. Specifically, different interfering signals contained in the contaminated EEG data are separated as different ICA components. After the ICA components of the interfering signals are removed, other ICA components may construct a corrected EEG data, thereby removing the interfering signals from the EEG signals. However, since the signal sources in human brain are dependent from each other, the ICA components associated with interfering signals usually contain some frequency band signals required for certain EEG analysis, such as α waveforms (alpha rhythm) generated when human brain relaxes. As a result, the EEG data is not useful for clinical diagnosis.

In light of the above problems, it is desired to provide an EEG signal processing method capable of preserving the frequency band signals required for EEG analyses after removal of the interfering signals.

SUMMARY OF THE INVENTION

It is therefore the primary objective of this invention to provide an EEG signal processing method that preserves required predetermined frequency band signals before removing interfering signals thereof.

The invention discloses an electroencephalogram signal processing method comprising a recording step, a retrieving step, a removing step and a synthesizing step. The recording step retrieves EEG signal components of a testee via a plurality of electrodes, wherein the EEG signal components serve as an input signal. The retrieving step filters the input signal to obtain a predetermined frequency band signal via a filtering unit, and subtracts the predetermined frequency band signal from the input signal to obtain a difference signal via a subtraction unit. The removing step performs an independent component analysis operation between the difference signal and a separating matrix to obtain an analysis signal via an analysis unit, generates a separating pseudo inverse and an independent analysis signal according to the separating matrix and the analysis signal respectively via a correction unit, and performs a matrix operation between the separating pseudo inverse and the independent analysis signal to obtain a corrected signal. The synthesizing step adds the corrected signal and the predetermined frequency band signal together to obtain an output signal via an addition unit.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

The term "couple" referred hereinafter means that two data processing units transfer data to each other via a data transfer interface for data transfer therebetween. The data processing units may be implemented by modular software, modular hardware or the combination thereof, as can be appreciated by one having ordinary skill in the art.

The term "separating matrix" referred hereinafter represents a matrix formed by independent signals separated from a received signal, as can be appreciated by one having ordinary skill in the art.

Figure 1:
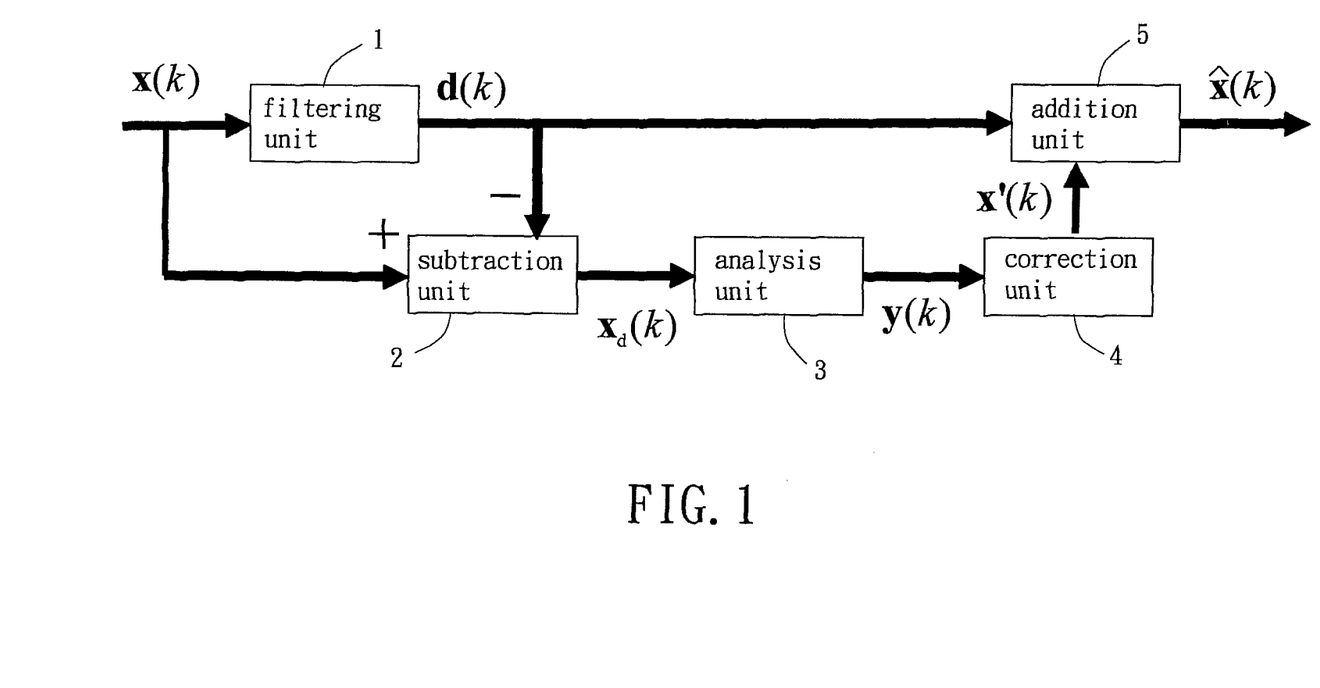
FIG. 1 shows a system performing an EEG signal processing method according to a preferred embodiment of the invention.

Referring to FIG. 1, a system performing an EEG signal processing method is shown according to a preferred embodiment of the invention. The system includes a filtering unit 1, a subtraction unit 2, an analysis unit 3, a correction unit 4 and an addition unit 5. The filtering unit 1 filters an input signal x(k) detected by a plurality of electrodes (not shown) to obtain a predetermined frequency band signal d(k). The subtraction unit 2 is coupled to the filtering unit 1 and performs a subtraction operation between the input signal x(k) and the predetermined frequency band signal d (k) to obtain a difference signal $x_d(k)$. The analysis unit 3 is coupled to the subtraction unit 2 and performs an independent component analysis (ICA) on the predetermined frequency band signal d(k) to obtain an analysis signal y(k). The correction unit 4 is coupled to the analysis unit 3 and corrects the analysis signal y(k) in order to remove interfering signals from the EEG signal components. Thus, a corrected signal x'(k) is generated by the correction unit 4. The addition unit 5 is coupled to the correction unit 4 and the filtering unit 1 and performs an addition operation between the corrected signal x'(k) and the predetermined frequency band signal d(k), thereby generating an output signal $\hat{x}(k)$. The filtering unit 1, the subtraction unit 2, the analysis unit 3, the correction unit 4 and the addition unit 5 can be implemented by the modular software, the modular hardware or the combination thereof, as can be appreciated by one having ordinary skill in the art. In this embodiment, the filtering unit 1, the subtraction unit 2, the analysis unit 3, the correction unit 4 and the addition unit 5 are implemented in term of the modular software by a device installed with a processing program and having numerical computation function and storage function (such as a computer or a digital signal processor (DSP)), but is not limited thereto.

Figure 2:
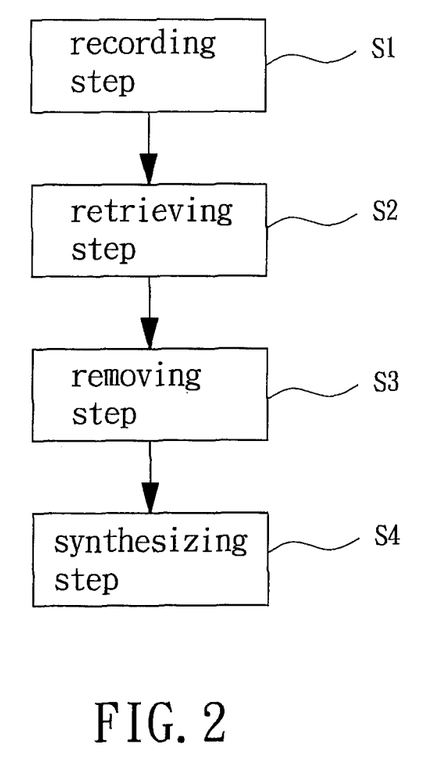
FIG. 2 shows a flowchart of the EEG signal processing method of the preferred embodiment of the invention.
Figure 3:
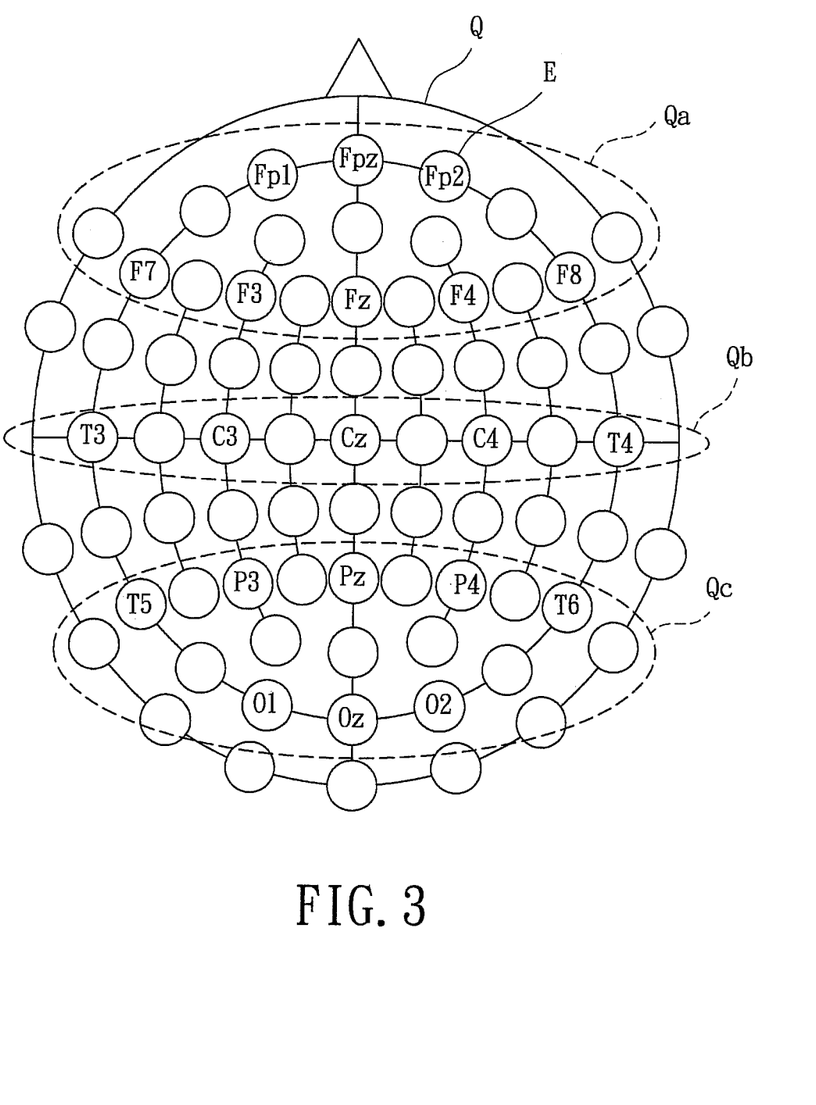
FIG. 3 is a top view of a human head covered with a plurality of electrodes.

Referring to FIGS. 1 and 2, a flowchart of the EEG signal processing method is shown. The flowchart includes a recording step S1, a retrieving step S2, a removing step S3 and a synthesizing step S4. The recording step S1 obtains EEG signal components of a testee via a plurality of electrodes, with the EEG signal components serving as the input signal x(k). In this embodiment, there are m electrodes. Referring to FIG. 3 also, the electrodes are shown to cover all over a scalp Q of the testee. In this case, the recording step S1 obtains the EEG signal components from the scalp Q of the testee via the plurality of electrodes E. Specifically, the EEG signal components are obtained from a frontal site Qa, a temporal site Qb and a rear site Qc of the scalp Q of the testee via the electrodes Fp1, Fpz, Fp2, F7, F3, Fz, F4, F8 (for the frontal site Qa), C3, Cz, C4, T3, T4 (for the temporal site Qb), T5, T6, P3, Pz, P4, O1, Oz and O2 (for the rear site Qc). The obtained EEG signal components are preferably magnified, sampled and quantified to form the input signal x(k), which is expressed by the formula below:

$$x(k)=[x_1(k),\ldots,x_m(k)]^T \quad (1),$$

wherein k is discrete time, m is the quantity of the electrodes, $[x_1(k), \ldots, x_m(k)]$ are EEG signal components obtained by the m electrodes, and $[x_1(k), \ldots, x_m(k)]^T$ is a transpose matrix of the signal matrix $[x_1(k), \ldots, x_m(k)]$.

Figure 4:
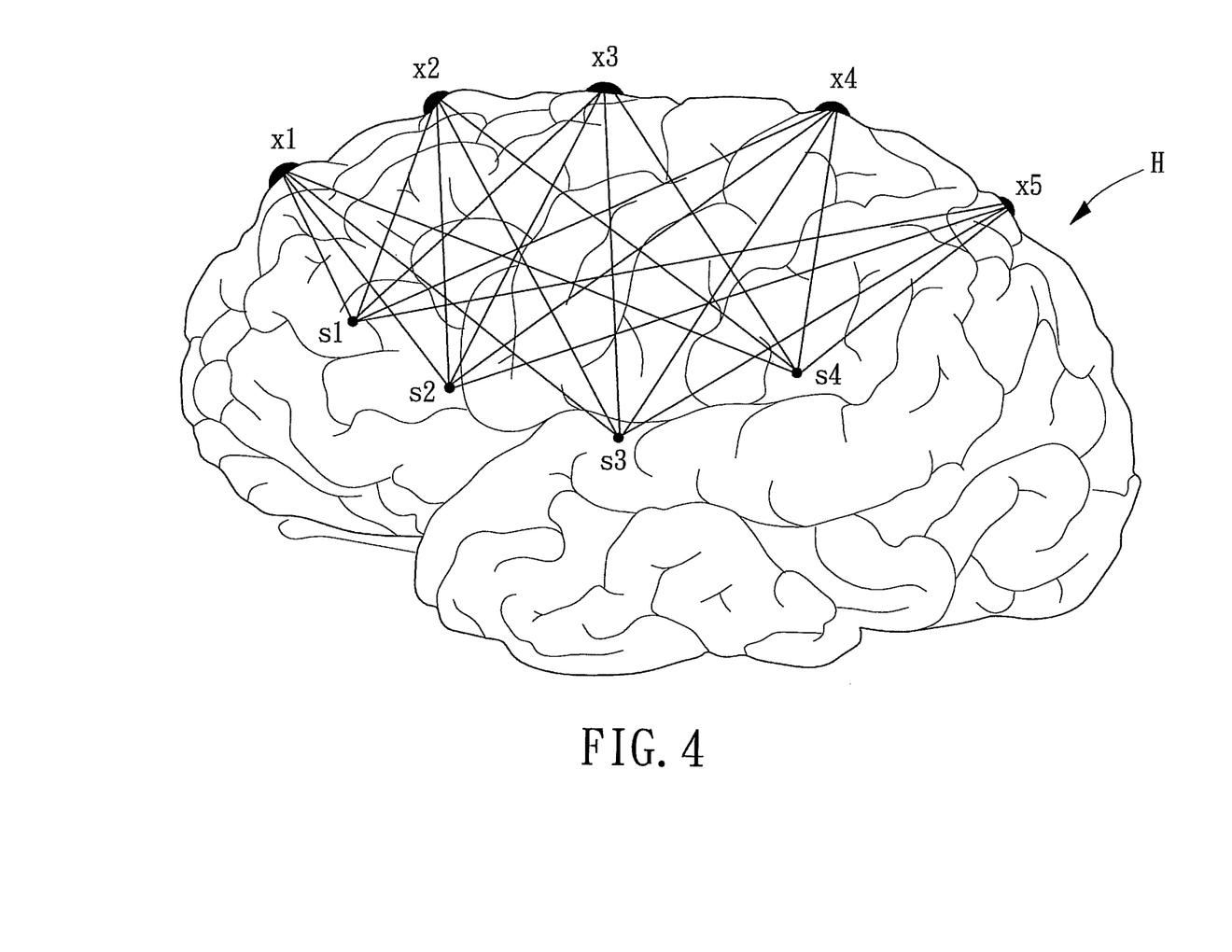
FIG. 4 shows original EEG signal components at various parts of a human brain.

FIG. 4 shows origins of EEG signal components. Since original EEG signal components s1, s2, s3 and s4 retrieved from the human brain H are easily contaminated by eye movement, blink, muscle movement, EKG or power line noises (not shown), the EEG signal components $x_1, x_2, x_3, x_4$ and $x_5$ retrieved by the electrodes may be represented in terms of a signal gain A and an interference factor v(k) after magnification, as shown in formula (2) and (3) below:

$$x(k)=As(k)+v(k) \quad (2),$$

$$s(k)=[s_1(k),\ldots,s_n(k)]^T \quad (3),$$

wherein A is a matrix of signal gain, and s(k) is a matrix of original EEG signal components. In this embodiment, n is 4, s1, s2, s3 and s4 are original EEG signal components retrieved from various parts of the human brain H, and v(k) is a unknown vector representing errors or noises.

The retrieving step S2 filters the input signal x(k) to obtain the predetermined frequency band signal d(k) via the filtering unit 1. Next, the subtraction unit 2 subtracts the predetermined frequency band signal d(k) from the input signal x(k) to obtain the difference signal $x_d(k)$ for the following removing step S3. In the embodiment, the filtering unit 1 is implemented as a conventional band pass filter (BPF) by the processing program, but is not limited thereto. Specifically, the retrieving step S2 filters the input signal x(k) to obtain the predetermined frequency band signal d(k) from the input signal x(k) via the filtering unit 1 for further storage. For example, a Fourier transform is performed on the input signal x(k) to convert the input signal x(k) into frequency domain. Predetermined frequency band signals are retrieved from the input signal x(k) under frequency domain and then converted into time domain signal as the predetermined frequency band signal d(k). In this embodiment, a waveforms of human brain are used as the predetermined frequency band signal d(k) for illustration purpose without taking it as a limited sense. In the following, the subtraction unit 2 subtracts the predetermined frequency band signal d(k) from the input signal x(k) to obtain the difference signal $x_d(k)$. The calculation of the subtraction unit 2 is expressed below:

$$x_d(k)=x(k)-d(k) \quad (4),$$

wherein k is discrete time.

The removing step S3 performs an ICA operation between the difference signal $x_d(k)$ and a separating matrix W to obtain the analysis signal y(k). Then, the correction unit 4 generates a separating pseudo inverse $(W)^+$ and an independent analysis signal y'(k) according to the separating matrix W and the analysis signal y(k) respectively, and performs a matrix operation between the separating pseudo inverse $(W)^+$ and the independent analysis signal y'(k) to obtain the corrected signal x'(k) for the following synthesizing step S4. Specifically, the removing step S3 performs the blind source separation of the ICA algorithm based on the difference signal $x_d(k)$ and the separating matrix w via the analysis unit 3. Namely, the removing step S3 performs an ICA operation to obtain the analysis signal y(k), as can be appreciated by one having ordinary skill in this art. The analysis signal y(k) can be obtained according to the following formula:

$$y(k)=Wx_d(k) \quad (5),$$

wherein k is discrete time. Next, the correction unit 4 performs a Moore-Penrose pseudoinverse operation on the separating matrix W to obtain the separating pseudo inverse $(W)^+$, and generates the independent analysis signal y'(k) based on independent waveforms of the analysis signal y(k). The rows of the independent analysis signal y'(k) representing interfering signals are set to zero, and a matrix operation is performed between the separating pseudo inverse $(W)^+$ and the independent analysis signal y'(k) to obtain the corrected signal x'(k). The corrected signal x'(k) can be obtained according to the following formula:

$$x'(k)=(W)^+ y'(k) \qquad (6),$$

wherein k is discrete time.

The synthesizing step S4 adds the corrected signal x'(k) and the predetermined frequency band signal d(k) together to obtain the output signal $\hat{x}(k)$ via the addition unit 5. The output signal $\hat{x}(k)$ can be obtained according to the following formula:

$$\hat{x}(k)=x'(k)+d(k) \qquad (7).$$

In the above formula (7), although the corrected signal x'(k) losses some useful information when the ICA algorithm operation is performed on the corrected signal x'(k) to remove interfering signals, the output signal $\hat{x}(k)$ can completely preserve the predetermined frequency band signal d(k) (while the conventional EEG signal processing method cannot do so) because the predetermined frequency band signal d(k) was obtained prior to the ICA algorithm operation and is added back to the corrected signal x'(k). Therefore, the invention can overcome the drawback of the convention EEG signal processing method where useful information contained in EEG signal components is lost after removal of interfering signals.

The improvement of the proposed EEG signal processing method applied to remove the interfering signals caused by ocular movement, muscle movement, EKG or line noises is described later in the specification. As shown in FIG. 3, a top view of a human head covered with the electrodes is shown. Various artifact sources that cause interfering signals are separately described below.

Figure 5A:
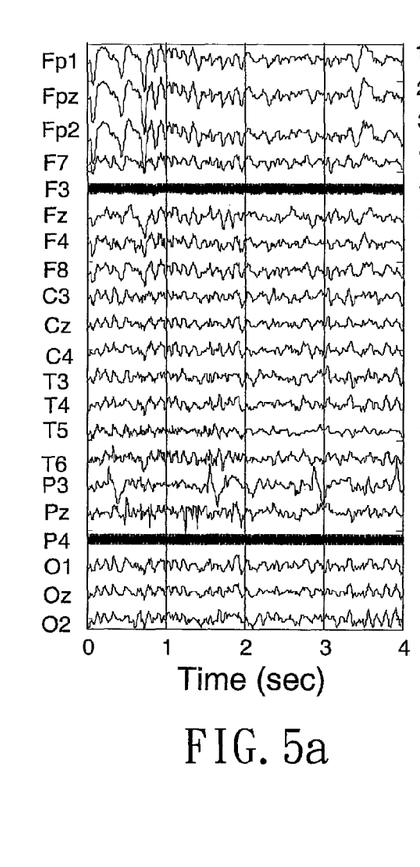
FIG. 5a shows EEG signal components contaminated by artifact sources.
Figure 5B:
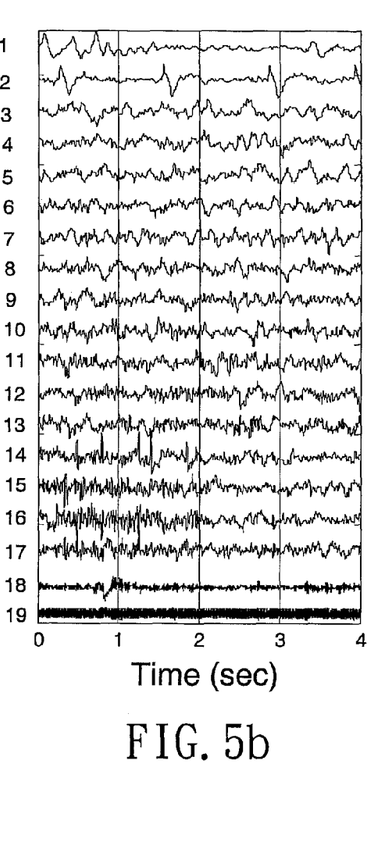
FIG. 5b shows EEG signal components after processing of an ICA operation.
Figure 5C:
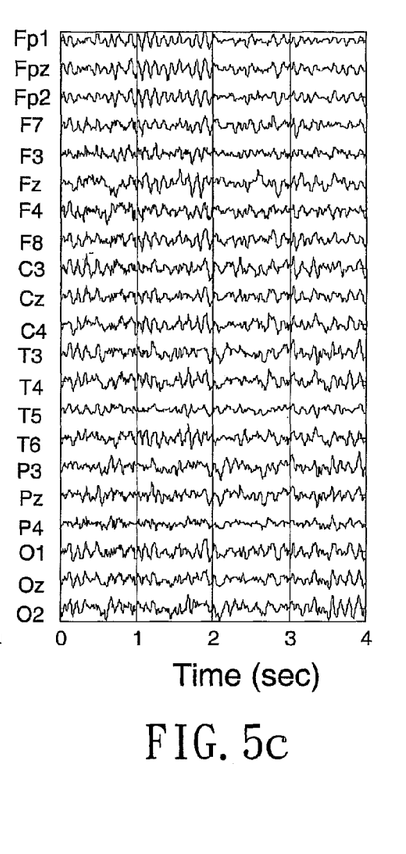
FIG. 5c shows EEG signal components corrected by the EEG signal processing method of the invention.

(A) Ocular Artifact Source:

FIG. 5*a* shows EEG signal components contaminated by an ocular artifact source. FIG. 5*b* shows EEG signal components after being processed by the ICA operation (namely, the resulted EEG signal components of conventional ICA-based EEG signal processing methods). FIG. 5*c* shows EEG signal components corrected by the EEG signal processing method of the invention. The EEG signal components contaminated by the ocular artifact source (as shown in FIG. 5*a*) are separated as an ICA component 1 shown in FIG. 5*b*. After correction of the proposed EEG signal processing method, it can be known from the EEG signal components (shown in FIG. 5*c*) detected by the electrodes E (numbered as Fp1, Fpz and Fp2) that the α waveforms near 10 Hz are masked by the ocular artifact source.

(B) Muscle Artifact Source:

Please refer to FIGS. 5*a*, 5*b* and 5*c* again, it can be known from the EEG signal components (shown in FIG. 5*a*) detected by the electrodes E (numbered as T5 and T6) that the interfering signals caused by the muscle movement exist between $0^{th}$ to $2^{nd}$ second and is separated as ICA components 15 and 16 shown in FIG. 5*b*. If the interfering signals are removed from certain rows of the independent analysis signal y'(k) in the removing step S3, it can be known from the FIGS. 5*a* and 5*c* that the signals of underlying EEG activities are obscured by the interfering signals of the rows caused by muscle movement.

(C) EKG Artifact Source:

Please refer to FIGS. 5*a*, 5*b* and 5*c* again, it can be known from the FIG. 5*a* that the interfering signals caused by the EKG appear in the EEG signal components detected by the electrode E (numbered as P3). The EEG signal components contaminated by the EKG artifact source (as shown in FIG. 5*a*) are separated as an ICA component 2. If the interfering signals caused by EKG are removed from certain rows of the independent analysis signal y'(k) in the removing step S3, the EEG signal components detected by the electrode E (numbered as P3) as shown in FIG. 5*c* may depict signals of underlying EEG activities after correction.

(D) Power Line Noise Artifact Source:

Please refer to FIGS. 5*a*, 5*b* and 5*c* again, it can be known from the FIG. 5*a* that the power line noise artifact source may be categorized into two categories. In the first category of the power line noise artifact source, the contaminated EEG signal components (as shown in FIG. 5*a*) detected by the electrodes E (numbered as F3 and P4) are separated as ICA components 18 and 19 shown in FIG. 5*b*. In the second category of the power line noise artifact source, the contaminated EEG signal components (as shown in FIG. 5*a*) detected by the electrode E (numbered as Pz) are separated as an ICA component 14 shown in FIG. 5*b*.

Moreover, because human brain generates α waveforms when human body is in relaxation, the level of relaxation of the testee can be determined based on whether the brain generates α waveforms or not. In the following, an example is made to illustrate that the EEG signal processing method of the invention is capable of processing α waveforms.

Figure 6A:
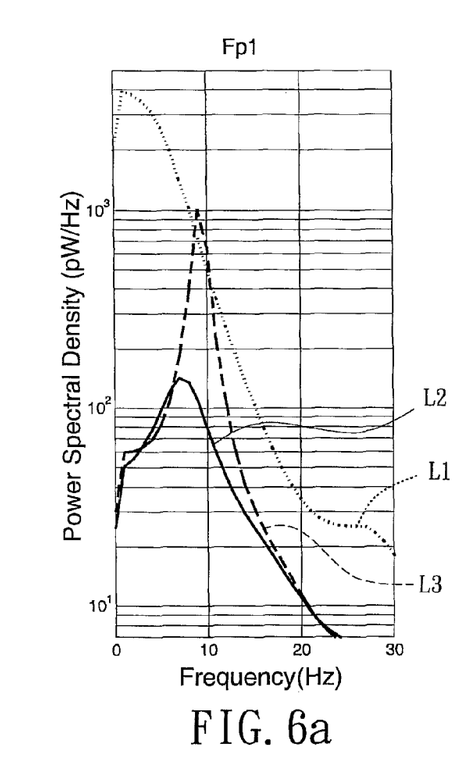
FIG. 6a shows frequency response curves of an electrode Fp1.
Figure 6B:
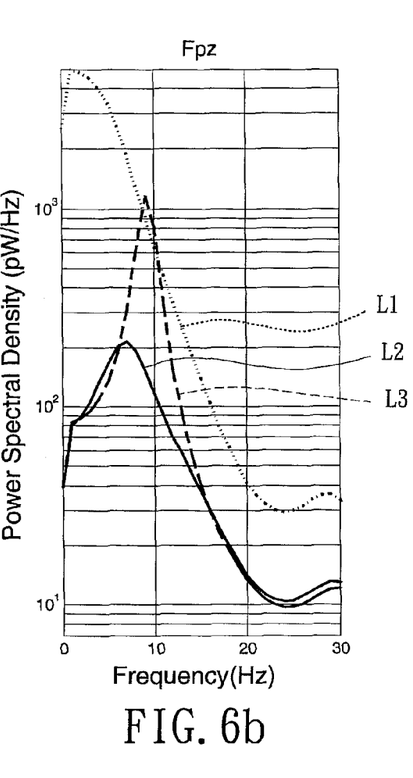
FIG. 6b shows frequency response curves of an electrode Fpz.
Figure 6C:
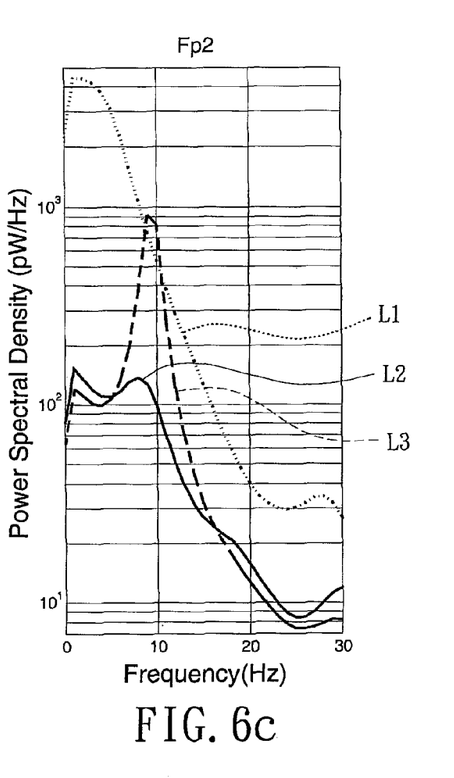
FIG. 6c shows frequency response curves of an electrode Fp2.

FIGS. 6*a*, 6*b* and 6*c* show frequency response diagrams of the electrodes Fp1, Fpz and Fp2, respectively. In the FIGS. 6*a*, 6*b* and 6*c*, L1 represents a curve of power spectral density (PSD) of contaminated EEG signal components, L2 represents a PSD curve of EEG signal components produced by conventional ICA-based EEG signal processing method, and L3 represents a PSD curve of EEG signal components produced by the proposed EEG signal processing method. It can be known from the FIGS. 6*a*, 6*b* and 6*c* that the EEG signal components corrected by the EEG signal processing method of the invention do not contain interfering signals caused by the ocular artifact source while preserving useful α waveforms (8 Hz to 13 Hz). In other words, the EEG signal processing method of the invention can efficiently preserve the a waveforms after removal of the interfering signals caused by artifact sources, as opposed to the conventional EEG signal processing method that causes the loss of a waveforms after removal of interfering signals.

Based on the above technical features, the EEG signal processing method of the invention is characterized as follows. First, the invention records EEG signal components of a testee as the input signal x(k) via the recording step S1. Second, the retrieving step S2 filters the input signal x(k) to obtain the predetermined frequency band signal d(k), and subtracts the predetermined frequency band signal d(k) from the input signal x(k) to obtain the difference signal $x_d(k)$. Third, the removing step S3 performs an ICA operation between the predetermined frequency band signal d(k) and the separating matrix W to obtain the analysis signal y(k), generates the separating pseudo inverse $(W)^+$ and the independent analysis signal y'(k) based on the separating matrix W and the analysis signal y(k) respectively, and performs a matrix operation between the separating pseudo inverse $(W)^+$ and the independent analysis signal y'(k) to obtain the corrected signal x'(k). Finally, the synthesizing step S4 adds the corrected signal x'(k) and the predetermined frequency band signal d(k) together to obtain the output signal $\hat{x}(k)$. Since the predetermined frequency band signal d(k) was obtained prior to the ICA algorithm operation, the output signal $\hat{x}(k)$ can be obtained by adding corrected signal x'(k) and the predetermined frequency band signal d(k) together.

Therefore, the output signal $\hat{x}(k)$ of the EEG signal processing method of the invention still contains the predetermined frequency band signal d(k), achieving preservation of useful frequency band signals required for certain brainwave analyses after removal of interfering signals. Thus, the invention achieves advantage of preserving required frequency band signals for various applications such as clinical diagnosis, distracted brainwave measurement, etc.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. An electroencephalogram signal processing method, comprising:
    a recording step retrieving EEG signal components of a testee via a plurality of electrodes, wherein the EEG signal components serve as an input signal;
    a retrieving step filtering the input signal to obtain a predetermined frequency band signal via a filtering unit, and subtracting the predetermined frequency band signal from the input signal to obtain a difference signal via a subtraction unit;
    a removing step performing an independent component analysis operation between the difference signal and a separating matrix to obtain an analysis signal via an analysis unit, generating a separating pseudo inverse and an independent analysis signal according to the separating matrix and the analysis signal respectively via a correction unit, and performing a matrix operation between the separating pseudo inverse and the independent analysis signal to obtain a corrected signal; and
    a synthesizing step adding the corrected signal and the predetermined frequency band signal together to obtain an output signal via an addition unit.

2. The electroencephalogram signal processing method as claimed in claim 1, wherein the input signal is expressed as $x(k)$, the input signal $x(k)=[x_1(k), \ldots, x_m(k)]^T$, k is discrete time, in is the quantity of the electrodes, $[x_1(k), \ldots, x_m(k)]$ is the EEG signal components retrieved by the electrodes, and $[x_1(k), \ldots, x_m(k)]^T$ is a transpose matrix of a matrix of the EEG signal components $[x_1(k), \ldots, x_m(k)]$.

3. The electroencephalogram signal processing method as claimed in claim 1, wherein the difference signal is expressed as $x_d(k)$, the difference signal $x_d(k)=x(k)-d(k)$, k is discrete time, $x(k)$ is the input signal, and $d(k)$ is the predetermined frequency band signal.

4. The electroencephalogram signal processing method as claimed in claim 1, wherein the analysis signal is expressed as $y(k)$, the analysis signal $y(k)=Wx_d(k)$, k is discrete time, W is the separating matrix, and $x_d(k)$ is the difference signal.

5. The electroencephalogram signal processing method as claimed in claim 1, wherein the corrected signal is expressed as $x'(k)$, the corrected signal $x'(k)=(W)^+y'(k)$, k is discrete time, $(W)^+$ is the separating pseudo inverse obtained by performing a Moore-Penrose pseudoinverse operation on the separating matrix, and $y'(k)$ is the independent analysis signal formed by independent waveforms of the analysis signal $y(k)$.

6. The electroencephalogram signal processing method as claimed in claim 1, wherein the output signal is expressed as $\hat{x}(k)$, the output signal $\hat{x}(k)=x'(k)+d(k)$, k is discrete time, $x'(k)$ is the corrected signal, and $d(k)$ is the predetermined frequency band signal.

* * * * *